United States Patent [19]
Manns et al.

[11] Patent Number: 5,910,450
[45] Date of Patent: Jun. 8, 1999

[54] PROCESS AND DEVICE FOR ENRICHING GAS, VAPOR AND/OR AEROSOL EMISSIONS RELEASED FROM AN OBJECT

[75] Inventors: Andreas Manns, Lübeck; Thomas Wuske, Malente; Dirk Zastrow; Sabine Grantz, both of Lübeck, all of Germany

[73] Assignee: Drägerwerk Aktiengesellschaft, Lübeck, Germany

[21] Appl. No.: 08/692,723

[22] Filed: Aug. 6, 1996

[30] Foreign Application Priority Data

Oct. 13, 1995 [DE] Germany ............... 195 38 075

[51] Int. Cl.⁶ ............ G01N 1/22; G01N 33/536; G01N 27/00; F26B 3/00
[52] U.S. Cl. ............ 436/181; 34/472; 436/536; 204/153.16
[58] Field of Search ............ 204/153.16; 436/536, 436/181; 34/472

[56] References Cited

FOREIGN PATENT DOCUMENTS

| | | |
|---|---|---|
| 0 304 304 B1 | 8/1988 | European Pat. Off. |
| 38 42 607 A1 | 6/1990 | Germany |
| 40 25 842 A1 | 12/1991 | Germany |

OTHER PUBLICATIONS

Iain L. Marr, Malcolm S. Cresser und Lambert J. Ottendorfer, 1988, Analytische Chemie für die Praxis, *Umweltanalytik*.

K. Figge, W. Rabel und A. Wieck, 1987, Adsorbents for the Enrichment of Organic Constituents of Air,*Fresenius Z. Anal Chem.*

Drägerwerk AG, 1994, Soil, Water, and Air Analyses as well as Industrial Gas Analysis, *Dräger Tube Handbook*.

P. Tijssen, Laboratory Techniques in Biochemistry and Molecular Biology, *Practice and Theory of Enzyme Immunoassays*.

Dr. rer.nat. Ursula Obst und Dr. rer.nat. Annette Holzapfel–Pschorn, 1988, Enzymatic Test for Water Analysis.

Jeanette M. Van Emon and Ralph O. Mumma, 1990, Immunochemical Methods for Environmentnal Analysis, *American Chemical Society*.

*Primary Examiner*—Frank C. Eisenschenk
*Assistant Examiner*—Hankyel T. Park
*Attorney, Agent, or Firm*—McGlew and Tuttle, P.C.

[57] ABSTRACT

A process for enriching substance emissions released from an object in the form of gases, vapors or aerosols, wherein the substance emissions are fed to an adsorption layer by diffusion or penetration and are enriched in the adsorption layer. The substance emission of an object is selectively detected according to the present invention by the adsorption layer being fixed on the surface of the object emitting pollutant, which surface is to be analyzed, by means of an adhesive tape projecting over the adsorption layer on all sides to offer adhesive surfaces for application to the object and to hermetically seal the adsorption layer against the ambient air. A nondestructive adsorption system is also provided, with direct or immediately following analysis for the rapid qualitative and/or quantitative determination of pollutants (e.g., gases, vapors, dusts) by means of a chemical or biological reaction, in which, e.g., specific biomolecules for selectively converting or selectively binding the collected or enriched pollutants and a system for displaying or identifying this conversion and/or binding are used.

23 Claims, 1 Drawing Sheet

PROCESS AND DEVICE FOR ENRICHING GAS, VAPOR AND/OR AEROSOL EMISSIONS RELEASED FROM AN OBJECT

FIELD OF THE INVENTION

The present invention pertains to a process for enriching gas, vapor and/or aerosol emissions released from an object, wherein the substance emissions are fed to an adsorption layer by diffusion or penetration and are enriched in the adsorption layer. The present invention also pertains to a nondestructive adsorption system with a direct or immediately following analysis for the rapid qualitative and/or quantitative determination of pollutants (e.g., gases, vapors, dusts) by means of a chemical or biological reaction, in which, e.g., specific biomolecules for the selective reaction or selective binding of the collected or enriched pollutants and a system for displaying or identifying this reaction and/or binding are used.

BACKGROUND OF THE INVENTION

Many of the objects in everyday use contain substances which become an objectionable potential pollutant due to continuous or intermittent release into the environment. They may be synthetic substances, such as plastics, synthetic resins or preservatives, or natural substances, such as mordants, oils or biocides. Of particular significance are the chemical compounds which occur either as gases, vapors, or in the solid form and may be bound by sorption on coarse or fine dusts, especially those environmental chemicals which increasingly occur as a pollutant load in the outdoor or indoor air of humans and animals. These are, e.g., formaldehyde, pentachlorophenol or pyrethroid pesticides, which may occur especially in furnishings of buildings and interior spaces, or in textile materials.

Objects, e.g., wooden components in structures or building structures, such as beams, ornaments, panelings, etc., as well as wooden objects and textiles, e.g., leather covers, are frequently inaccessible to a direct analysis, because they are too large, too bulky, or too costly. Even if the analysis of these objects is possible, it is usually very expensive or difficult with respect to the emission of pollutants. In this case, it is necessary to take samples of the objects, and the samples are then tested irreversible destructively, i.e., the so-called substance samples are subjected to a consuming chemical or physical processing, i.e., destruction, in the course of the analysis, and they cannot be returned to the place from where they were taken. Furthermore, only the pollutant potential can be determined by such a consuming analysis. Data on the actual release of the potentially harmful substances into the environment can be obtained only indirectly at best.

In contrast, hundreds of organic compounds, which are frequently of anthropogenic origin, can be detected in the atmosphere, besides the inorganic compounds (CO, $NO_x$, $SO_2$, etc.), which occur at even higher concentrations (cf. I. L. Marr, M. S. Cresser, L. J. Ottendorfer: *Analytische Chemie für die Praxis: Umweltanalytik* [Analytical Chemistry for Practice: Environmental Analysis], Georg Thieme Verlag, Stuttgart, 1988). The following methods have been known from the state of the art for enriching these organic constituents of air, which usually occur at low concentrations in the form of gases, vapors and/or aerosols:

1. Physical or chemical adsorption in liquids,
2. Condensation at low temperatures (freezing out), and
3. Adsorption on solids.

One major drawback of the adsorption method is that the organic constituents of air, which occur in trace concentrations, can be quantified only inaccurately in the liquid adsorbents. Losses, which distort the result, are unavoidable during concentration.

Condensation is suitable predominantly only for especially high mass concentrations and components having a relatively high vapor pressure. It is disadvantageous here that the water vapor present is also condensed and may interfere with the subsequent chemical analysis.

In contrast, various practical methods of adsorptive enrichment have proved to be successful. However, a direct analysis is not possible in this case, either, because elution or thermal desorption of the analytes collected is inevitable in most cases before the analysis proper. The chemical and physical properties of the various adsorbents lead to a less stable retention of the lower-boiling constituents of air, i.e., to an earlier breakthrough of the compounds through the layer of adsorbent, as a consequence of which a quantitative determination will become uncertain (cf. K. Figge, W. Rabel, and A. Wieck: Adsorbents for the Enrichment of Organic Constituents of Air, *Fresenius Z. Anal. Chem.,* Vol. 327 (1987), pp. 251–278).

To obtain data on the concentration in the evaluation of an analysis, the substance to be measured must be brought to the adsorbent in a defined manner during the enrichment. Sampling methods for enriching substance emissions released from objects emitting pollutants when the substance admissions are fed to an adsorption layer by defusing or penetration and are enriched in the adsorption layer by adsorption have been known from, e.g., *Dräger-Röhrchen Handbuch: Boden-, Wasser-und Luftuntersuchung sowie technische Gasanalyse* [Dräger Tube Handbook: Soil, Water, and Air Analyses as well as Industrial Gas Analysis], 8th edition, Lübeck, 1991.

Systems with so-called active sampling and passive sampling methods are distinguished. The enriched air volume is the decisive reference quantity for the subsequent calculation of the concentration in the active system. Passive systems are designed, in general, for sampling over longer periods of time and for determining average concentrations or shift mean values. In contrast, the instantaneous environmental concentration is determined in the case of an active sampling. However, both methods fail to furnish any information on or are not directly related to the actual source emitting or releasing the pollutant, but they are sensitive to the room air only.

Processes and devices for collecting gases, especially formaldehyde, by sorption for enriching substance emissions released from objects emitting pollutants when the substance admissions are fed to an adsorption layer by defusing or penetration and are enriched in the adsorption layer by adsorption have been known from DE-A-38 42 607 and DE-A-40 25 842. However, these processes are also limited to the adsorption of gases present in the room air. Object-related sampling cannot be performed.

SUMMARY AND OBJECTS OF THE INVENTION

This is where the present invention fits in, whose basic object is to provide a process with which a punctiform, object-related sampling can be performed. According to advantageous embodiments, it is also possible to perform direct analyses, which can be standardized, and can be carried out rapidly and in a simple manner, and nondestructively for the goods and objects to be analyzed.

Another object of the present invention is to collect constituents of air, which may occur in room air as potential pollutants in the form of gases, vapors and/or bound to particles, directly at the object emitting them in a nondestructive manner, and to detect them directly or immediately thereafter by means of, e.g., highly selective and sensitive reactions, e.g., biochemical reactions. Another object of the present invention is to provide a device for carrying out the process.

The object is accomplished according to the present invention by using an enriching process in which the substance to be detected can be enriched in an adsorption layer by both diffusion and penetration, wherein the adsorption layer is fixed directly on the surface of the object to be investigated. The adsorption layer is attached to the surface of the object, which projects over the adsorption layer on all sides, by means of an adhesive tape. A small sampling space is thus generated on the surface of the object, and it is hermetically sealed against the environment. As a result, the analyte to be detected can be directly attributed to a source or emission site.

The fact that the analyte is fixed on an adsorbent due to penetration and/or diffusion has proved to be especially successful in this connection. The adsorption layer provided for this purpose may at the same time be coupled according to the present invention with a reaction layer and/or a signal converter, so that the analyte can be detected in situ. According to another variant of the present invention, the sampling device may be designed such that a chemical and/or biochemical reaction, e.g., electrochemical or immunochemical reaction, which immediately follows the sampling proper, is performed.

Biochemical analyses, so-called enzyme assays and immunoassays, are highly sensitive test systems for the qualitative and/or quantitative determination of compounds based on the enzyme-substrate or antibody-antigen reaction. Homogeneous and heterogeneous systems are distinguished among the immunoassays. Depending on the mode of execution and the components, a classification into so-called competitive, noncompetitive, or sandwich tests may be made here as well. These variants are known to the person skilled in the art and are described in the literature (cf. P. Tijssen, *Laboratory Techniques: Practice and Theory of Enzyme Immunoassays*, Vol. 15, Elsevier Science Publishers B. V., Amsterdam, 1985, as well as C. P. Pierce and D. J. Newman: *Principles and Practice of Immunoassays*, Stockton Press, New York, 1991).

Immunoassays and enzyme reactions have recently also been used successfully to determine environmental chemicals in soil and water samples (cf. U. Obst and A. Holzapfel-Pschorn: *Enzymatische Tests für die Wasseranalytik* [Enzymatic Tests for Water Analysis], R. Oldenbourg Verlag, Munich, 1988, and J. van Emon and R. O. Mumma: Immunochemical Methods for Environmental Analysis, *ACS Symposium Series* 442, AS Washington, 1990). Their use in the analysis of constituents of air opens up the possibility of detecting pollutants which cannot be measured directly or can be measured by the currently usual physical and chemical methods only by means of expensive enriching, derivatization and analytical processes. The advantage of the use of biochemical processes for the analysis of air-borne pollutants is that these processes have meanwhile been simplified in terms of the composition of their components, handling and performance, so that they can be used on site even by nonexperts. This makes possible direct measurements or monitoring, e.g., at the workplace, in the home or in interior spaces. Biochemical detection reactions are also characterized by being extremely substance-sensitive and -selective. Thus, the enriched amounts needed are small and the enrichment times needed are short, and the detection limits are very low. This can be considered to be an added advantage over the prior-art chemical and physical analytical methods.

The analytes suitable in connection with the present invention include, in principle, all compounds whose vapor pressure causes a saturation concentration sufficient for the process described here, or solid compounds which demonstrably penetrate into the reaction layer via the contact surface and are enriched.

The hermetic sealing of the sampling space by means of an adhesive tape proved to be particularly advantageous within the scope of the present invention. The adhesive tape is able to adapt itself to the nature of the surface of the body or object and to tightly seal same against its environment. This makes possible the exclusive detection of evaporation or gas release processes which occur on a defined surface. The total emission of substances or compounds relative to the total surface of the object can be determined from the dimensions of the adhesive tape geometry, the roughness of the body being measured, and the defined surface of the object. Due to the planar geometry of the adhesive tape according to the present invention, the volume needed for the analysis is extremely small, in the $\mu L$ range. This is also favorable for a rapid on-site analysis, because saturation concentrations are reached more rapidly in the vapor space as the volume decreases.

Another advantage of the process according to the present invention is that the chemical or physical environmental effects, which cause changes in the adsorbate over time, are not manifested.

Various, commercially available filter materials made of glass fibers, cellulose nitrate, plastics, aluminum oxide, silica gel, and other materials have proved to be suitable adsorption layers. The nature of the layer depends on the analyte to be adsorbed and the subsequent reaction steps in the analytical procedure.

It was surprisingly possible to show that in a preferred application, the adsorption layer and the reaction layer may be identical. If the analysis is based on a biochemical reaction, the reaction layer is in a porous polymer matrix (gel), whose pores are filled with water or an organic solvent. This polymer matrix is used now as a carrier for the biochemical reaction components and is at the same time the site of the biochemically catalyzed signaling. Should it be necessary to store individual reactants separately, it is possible, e.g., to design the reaction layer as a multiple layer. At the beginning of a measurement, the individual layers or compartments are to be brought together or to be activated by means of an activation step, e.g., the removal of a protective film, breaking of an ampule, moistening with an atomizer, etc.

In another embodiment of the present invention, the adsorbed analyte may be solubilized in the reaction layer, e.g., the polymer matrix, via the contact surface of the adsorbent, and it can thus be made directly accessible to the subsequent chemical or biochemical detection reaction.

If a coupled enrichment and analysis of the substance is not possible, the device according to the present invention may be used as a simple collection unit. The adsorption layer of the surface of the subject is exposed in this case as well. This adsorption layer may be chemically or biochemically derivatized, similarly to EP-A-0 304 304. The analyte collected can be converted into a perceptible signal as a consequence of one or more subsequent process steps, and this signal can be read on the adsorption layer. The process steps meant in this connection are, e.g., washing, incubation, filtration, and/or derivatization steps. If the device according to the present invention is used simply as an adsorption layer, the adsorption layer can also be subjected to a prior-art analysis, such as GC, HPLC, TLC, or GC-MS, after suitable processing for the particular analysis. This is especially meaningful if many analytes are emitted and cannot be analyzed and quantified without time-consuming and expensive measurements.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
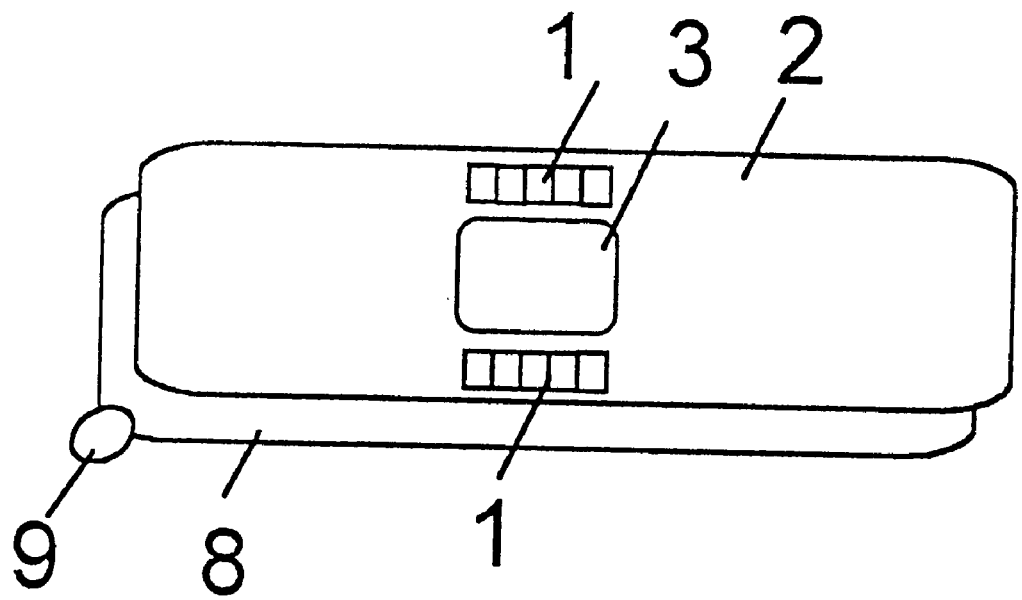
FIG. 1 is a schematic view of a nondestructive sampling and analytical unit.
Figure 2:
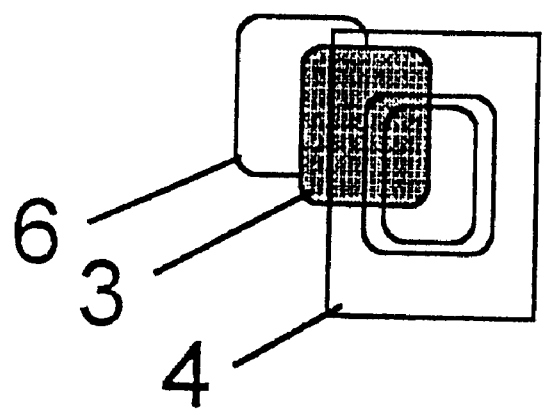
FIG. 2 is a schematic view of the layer structure of the sampling and analytical unit.

On the whole, the sampling and analytical unit comprises a contact adhesive layer 2, which is coated with adhesive on one side, and in which a color reference scale 1 is attached on the adhesive-free surface facing away from the surface of the object, and in which the adsorption layer 3 is applied to the surface facing the surface of the object. Mounted reversibly, an impermeable protective film 8 is located on the underside; this protective film 8 is not transparent to light and is removed before use and it makes the adhesive surface 2 and the adsorption layer 3 accessible for the collection and measurement proper. To facilitate the removal of the protective film 8, it may have, e.g., special bulging parts 9 for pulling. If only gases or vapors are to be collected, a chemically inert spacer 6, which is permeable to the analytes, is arranged in front of the adsorption layer 3. A defined diffusion path is thus set between the planar sample and the adsorption layer, and direct contact with the sample surface is prevented. If migrating particles are also to be sorbed besides gases and vapors in the case of penetration sampling, the spacer 6 must be omitted.

Reaction components and signal conversion components may be additionally integrated in the above-described adsorption layer 3. The spacer may assume additional protective and contrast functions, as in a colorimetric analytical unit. An analytical window 4 on the side facing away from the object makes it possible to directly visualize a signal generated in the adsorption layer 3. The analytical window 4 is integrated in the adhesive contact layer 2 by means of a border.

EXAMPLES

Key to the abbreviations used in the following examples:
PBS buffer: 35.1 g of NaCl+4.72 g of $Na_2HPO_4$+0.92 g of $NaH_2PO_4$ made up to 4 L with $H_2O$, pH value: 7.4
TMB coloring solution: 1 mL of dioctylsulfosuccinate 0.8% (w/w) in ethanol, 40 $\mu$L of TMB 6% (w/w) in DMSO, 4 mL of 50-mM acetate buffer, pH value: 5.0, 3 $\mu$L of $H_2O_2$, 35%
PBS washing buffer: 0.15M NaCl, 0.002M $NaH_2PO_4$—$H_2O$, 0.008M $Na_2HPO_4$, 0.05% (v/v) Tween 20, pH value=7.4

Example 1

Determination of Formaldehyde in a Wood Sample

A gel layer was prepared as the adsorption reaction layer for the enzymatic determination of formaldehyde.

1.1. Preparation of an Enzymatically Active Device

To prepare the reaction layer (20-mL batch), a transparent carrier material was mixed with 20 mL of 50-mM potassium phosphate buffer (pH value 7.8) and heated at 700 W in a microwave generator. It was subsequently cooled to 46° C. in a water bath. 0.2 g of trehalose, 14.2 g of NAD-Li, 10 mg of INT, 50 mU of diaphorase, or alternatively 1 $\mu$mole of 1-methoxyphenazine sulfate, and 50 mU/mL of formaldehyde hydrogenase from *Pseudomonas putida* were added while stirring gently after cooling. Two hundred $\mu$L of the liquid gel thus prepared were poured into a deep-drawn mold made of thermoplastic polyester glycol (PETG).

The geometry of the molding determines the thickness of the reaction matrix (the layer thickness was 2 mm here), the surface to be analyzed (1 $cm^2$ here in the planar state), as well as the size of the inspection window (1 $cm^2$ in this case). The gel can be stored at 4° C. after hardening, in general, e.g., packed airtightly in the mold, or it is directly installed as an adsorption reaction layer between the support layer and the contrast layer made of a two-ply polyester mat (0.5 mm, firm of Lohmann, No. 0980) and the transparent molding, which acts as a mount and inspection window.

Besides agarose as the polymer matrix forming the adsorption reaction layer, it is also possible to use other organic or inorganic preparations within the scope of the present invention.

1.2. Enrichment and Analysis

The devices prepared according to 1.1. were bonded to a wooden surface for a period ranging from 0.25 to 24 hours. Formaldehyde diffused to the surface of the adsorption reaction layer. A combined catalytic reaction of the enzymes formaldehyde dehydrogenase (EC 1.2.1.46) and diaphorase (EC 1.6.99) together with a color-producing system (cf. DE 37 205 064) was used to detect formaldehyde emissions.

Depending on the amount of formaldehyde emitted from the object, it was possible to observe a gradual change in the color of the hydrogen through the transparent molding. The color values obtained were assigned to the corresponding amounts of formaldehyde by means of a calibrated color strip. In addition, it was also possible to relate this measured value to the surface of the object defined by the geometry of the device (2 $cm^2$ in this case).

Example 2

Collection of PCP with Subsequent Conventional Analysis 2.1. Preparation of a Device for Collecting PCP The device for passively collecting PCP comprised an adhesive contact layer, with which the analytical window was hermetically sealed. A circular glass fiber filter (diameter 10 mm) was bonded in the center of the adhesive contact layer. Besides the glass fiber filter as the adsorption layer, it was also possible to use divinylbenzene copolymers, methacrylates, activated carbons, and other sorbents, which sorb organic chlorinated hydrocarbons of low volatility. A perforated screen disk made of chemically inert stainless steel (diameter 12 mm) was positioned between the object to be analyzed and the glass fiber filter, because a defined, rigid diffusion path was to be set. The spacer was also placed on the adhesive contact layer.

2.2. Enrichment and Analysis

The device was bonded to wood and incubated over a period of 2 to 16 hours. The device was pulled off, and the sorbent disk used was extracted in 2 mL of a 50-mM PBS-Tween 20 solution (0.01%) at a pH value of 9.4 for 10 minutes at 35° C. in an ultrasonic bath.

Besides this extraction instruction, it is also possible to use solvents or solvent mixtures known to the person skilled in the art. In this case, the extract should be subsequently diluted with PBS-Tween 20 (0.01%) at a ratio of 1:500 before a correspondingly adapted immunochemical test is performed.

The extract was subsequently filtered on a filter (cut-off 0.45 μm) to remove all particles. Various dilutions of this extract were subjected to quantitative analysis for their PCP concentration within the framework of a PCP-specific immunochemical test.

Example 3

Device for Determining PCP in a Wood Sample 3.1. Preparation of the Immunochemically Active Device The anti-PCP antibodies described by Duquette et al. (1991) and PCP tracer were used as the specific reaction components. Since the specific anti-PCP antibodies should be immobilized on the reaction layer, membranes, which permit a direct covalent or sorptive binding between relatively inert membrane or filter material, such as glass fiber filter, and antibodies, were especially suitable (cf. Sigrist et al., 1992). Plastic membranes and glass fiber filters were used as the adsorption layer 3 in the process example described, because they were well suited for the covalent binding of the above-mentioned type, possessed good mechanical properties, and the immobilization of the antibodies on them was able to be performed in a simple manner. The antibodies were applied to the membranes by means of, e.g., a pipette. Following the coating with antibodies, the carrier layer was saturated in a 0.1% (w/w) casein solution to prevent the nonspecific binding of components of the solution to the layer/filter during the further incubation steps. The adsorption layer was dried at room temperature after the saturation step. The layer thus pretreated was subsequently placed into/onto the device. The device thus prepared was now able to be used for the nondestructive sampling and the subsequent analysis.

3.2. Enrichment and Analysis

The devices prepared according to 3.1. (e.g., Immunodyne® 3.0 filter) were placed on wood samples, reinforced with a round filter (diameter 90 mm) as the support layer 6 on the side facing away from the sampling, and wrapped around with a film (as a substitute for the adhesive surface 2). The object was sampled for 5 hours at room temperature in darkness. The adsorption layer 3 was incubated for 20 minutes in 2 to 3 mL of a conjugate solution diluted at 1:10,000 in PBS buffer for the subsequent analysis, and then washed 5 times in PBS buffer. The adsorption layer then became the reaction layer by adding, per unit, 2.4 mL of coloring solution and incubating at room temperature. The reaction was subsequently terminated by means of the reagents known to the person skilled in the art, and it was able to be evaluated.

What is claimed is:

1. A process for enriching substance emissions released from an object emitting pollutants in the form of gases, vapors and aerosols, the object having a surface, the process comprising the steps of:

providing an adsorption layer;

fixing said adsorption layer on the surface of the object emitting pollutants, which is to be analyzed, by means of an adhesive tape projecting over the adsorption layer on all sides, to offer adhesive surfaces for application to the object and to hermetically seal the adsorption layer against the ambient air;

feeding substance emissions to said adsorption layer by diffusion or penetration; and enriching the substance emissions in the adsorption layer by adsorption.

2. A process in accordance with claim 1, wherein the enriched substance emission is converted into a perceptible signal by means of a chemical reaction.

3. A process in accordance with claim 1, wherein the enriched substance emission is converted into a perceptible signal by means of a biological reaction.

4. A process in accordance with claim 2, wherein the enriched substance emission is converted into a perceptible signal by means of an electrochemical reaction.

5. A process in accordance with claim 2, wherein the enriched substance emission is converted into a perceptible signal by means of an assay selected from the group consisting of an enzyme assay and immunoassay.

6. A process in accordance with claim 2, wherein the reaction takes place directly on the adsorption layer.

7. A process in accordance with claim 3, wherein the reaction takes place directly on the adsorption layer.

8. A process in accordance with claim 4, wherein the reaction takes place directly on the adsorption layer.

9. A process in accordance with claim 5, wherein the reaction takes place directly on the adsorption layer.

10. A process in accordance with claim 2, wherein the reaction takes place during the collection of the substance emission.

11. A process in accordance with claim 3, wherein the reaction takes place during the collection of the substance emission.

12. A process in accordance with claim 2, wherein the substance emission collected is converted as a consequence of one or more process steps, selected from the group consisting of washing, incubation, filtration and derivatization, into a perceptible signal, which can be read on the adsorption layer.

13. A process in accordance with claim 3, wherein the substance emission collected is converted as a consequence of one or more process steps, selected from the group consisting of washing, incubation, filtration and derivatization, into a perceptible signal, which can be read on the adsorption layer.

14. A process in accordance with claim 1, wherein said adsorption layer is formed of a filter material selected from the group consisting of glass fibers, cellulose nitrate, plastics, aluminum oxide, and silica gel;

a color reference scale is provided, and qualitative and quantitative determination of the emissions is performed by comparing said adsorption layer with said color reference scale.

15. A process in accordance with claim 1, wherein said substance emissions are collected from objects emitting pentachlorophenol or formaldehyde.

16. A device for collecting substance emissions released from objects emitting pollutants in the form of one of gases, vapors and aerosols, comprising:

a flexible plastic support with a contact adhesive layer coated with an adhesive on one side; and an adsorption layer with an adsorption portion adapted to taking up the substance emission, the adsorption layer comprising a filter material selected from the group consisting of glass fibers, cellulose nitrate, plastics, aluminum oxide, and silica gel, said adsorption layer having means for collecting and enriching the emissions.

17. A device in accordance with claim 16, wherein the adsorption layer contains optical signal means for converting the emission into an optical signal.

18. A device in accordance with claim 17, wherein said optical signal means is located directly in the adsorption layer.

19. A device in accordance with claim 17, wherein said optical signal means includes a reaction layer present in a porous polymer matrix, whose pores are filled with water or an organic solvent, wherein the polymer matrix is also the carrier of biochemical reaction components.

20. A device in accordance with claim 16, further comprising a spacer arranged on said adsorption layer such that it maintains said adsorption layer separated in space from the object surface to be analyzed.

21. A device in accordance with claim 16, further comprising flexible adhesive tape projecting over the adsorption layer on all sides to hermetically seal the adsorption layer from the ambient air;

a color reference scale positioned adjacent said adsorption layer for qualitative and quantitative determination of the emissions.

22. A process for detecting emissions released from an object, comprising the steps of: using a flexible adhesive tape with a contact adhesive layer coated with an adhesive on one side and with an adsorption layer arranged on it for detecting a substance emission released from an object, and positioning the tape with adsorption layer on the object;

converting emissions released from the object into a perceptible signal.

23. A process for enriching substance emissions released from an object emitting pollutants, such as building parts, furnishings of interior spaces or textile materials, in the form of gases, vapors and aerosols, the object having a surface, the process comprising the steps of:

providing an adsorption layer;

fixing said adsorption layer on the surface of the object emitting pollutants, which is to be analyzed, by means of an adhesive tape projecting over the adsorption layer on all sides, to offer adhesive surfaces for application to the object and to hermetically seal the adsorption layer against the ambient air;

providing a spacer between said adsorption layer and the surface of the object, said spacer separating said adsorption layer from the surface of the object and blocking direct contact between said adsorption layer and the surface, said spacer blocking migration of particles from the surface to said adsorption layer, said spacer passing gases from the surface to said adsorption layer;

feeding substance emissions to said adsorption layer though said spacer by diffusion or penetration; and enriching the substance emissions in the adsorption layer by adsorption.

\* \* \* \* \*